United States Patent
Jonckers et al.

(10) Patent No.: US 8,552,021 B2
(45) Date of Patent: Oct. 8, 2013

(54) PHOSPHORAMIDATE DERIVATIVES OF NUCLEOSIDES

(75) Inventors: Tim Hugo Maria Jonckers, Edegem (BE); Pierre Jean-Marie Bernard Raboisson, Beerse (BE); Koen Vandyck, Paal-Beringen (BE); Michael Pelcman, Huddinge (SE); Bengt Christian Sund, Huddinge (SE); Horst Jurgen Wahling, Huddinge (SE); Pedro Manuel Passos Pinho, Huddinge (SE); Anna Winqvist, Huddinge (SE); Karl Magnus Nilsson, Huddinge (SE)

(73) Assignees: Janssen Products, L.P., Horsham, PA (US); Medivir AB, Huddinge (SE)

( * ) Notice: Subject to any disclaimer, the term of this patent is extended or adjusted under 35 U.S.C. 154(b) by 0 days.

(21) Appl. No.: 13/498,459

(22) PCT Filed: Sep. 29, 2010

(86) PCT No.: PCT/EP2010/064413
§ 371 (c)(1),
(2), (4) Date: Mar. 27, 2012

(87) PCT Pub. No.: WO2011/039221
PCT Pub. Date: Apr. 7, 2011

(65) Prior Publication Data
US 2012/0225839 A1   Sep. 6, 2012

(30) Foreign Application Priority Data
Sep. 29, 2009  (EP) .................................... 09171607

(51) Int. Cl.
*A61K 31/506* (2006.01)
*C07F 9/06* (2006.01)

(52) U.S. Cl.
USPC .......... 514/274; 544/242; 544/243; 536/28.1; 536/28.4; 514/256; 514/269

(58) Field of Classification Search
USPC ............... 544/242, 243; 514/43, 49, 51, 256, 514/274; 536/28.1, 28.4
See application file for complete search history.

(56) References Cited

U.S. PATENT DOCUMENTS

| | | | |
|---|---|---|---|
| 7,453,187 B2 | 11/2008 | Richards et al. | |
| 7,666,856 B2* | 2/2010 | Johansson et al. | 514/51 |
| 7,825,239 B2* | 11/2010 | Kalyanov et al. | 536/28.53 |
| 7,935,681 B2* | 5/2011 | Johansson et al. | 514/51 |
| 7,964,580 B2* | 6/2011 | Sofia et al. | 514/51 |

FOREIGN PATENT DOCUMENTS

| | | |
|---|---|---|
| EP | 0858833 B1 | 3/2003 |
| EP | 0842276 B1 | 1/2004 |
| EP | 1037974 B1 | 3/2007 |
| WO | 2007020193 A2 | 2/2007 |
| WO | WO2008043704 A1 | 4/2008 |
| WO | WO2009067409 A1 | 5/2009 |

OTHER PUBLICATIONS

Rondla et al (2009): STN International HCAPLUS database, Columbus (OH), accession No. 2009: 1507900.*
Krieger, et al, May 1, 2001, Enhancement of Hepatitis C Virus RNA Replication by Cell Culture, Journal of Virology, 75-10, 4614-1624.
Lohmann, et al., 1999, Replication of Subgenomic Hepatitis C Virus RNAs in a Hepatoma Cell Line, Science, vol. 285, pp. 110-113.
Smith, et al., "The Design, Synthesis, and Antiviral Activity of 4'-Azidocytidine Anallogues against Hepatititis C Virus Replication: The Discovery of 4'-Azidoarabinocytidine", J. Med. Chem., vol. 52, pp. 219-223, 2009.

* cited by examiner

*Primary Examiner* — Golam M M Shameem

(57) ABSTRACT

Compounds of formula I:

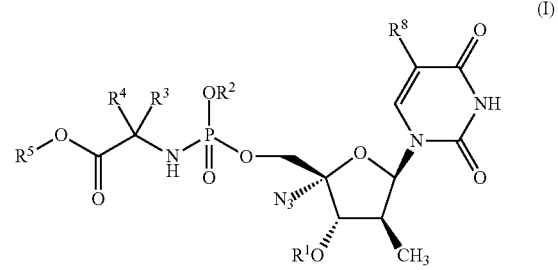

including any possible stereoisomers thereof, wherein:
$R^1$ is hydrogen, —C(=O)$R^6$ or —C(=O)CHR$^7$—NH$_2$;
$R^2$ is hydrogen; or $C_1$-$C_6$alkyl or phenyl, either of which is optionally substituted with 1, 2 or 3 substituents each independently selected from halo, $C_1$-$C_6$alkyl, $C_2$-$C_6$-alkenyl and $C_1$-$C_6$alkoxy, hydroxy or amino, or $R^2$ is naphtyl; or $R^2$ is indolyl,
$R^3$ is hydrogen, $C_1$-$C_6$alkyl, benzyl;
$R^4$ is hydrogen, $C_1$-$C_6$alkyl, benzyl; or
$R^3$ and $R^4$ together with the carbon atom to which they are attached form $C_3$-$C_7$cycloalkyl;
$R^5$ is $C_1$-$C_{10}$alkyl, $C_3$-$C_7$-cycloalkyl, benzyl, or phenyl, any of which being optionally substituted with 1, 2 or 3 substituents each independently selected from hydroxy, $C_1$-$C_6$alkoxy, amino, mono- and di$C_1$-$C_6$alkylamino;
$R^6$ is $C_1$-$C_6$ alkyl;
$R^7$ is $C_1$-$C_6$ alkyl;
$R^8$ is hydrogen or halogen;
or a pharmaceutically acceptable salt or solvate thereof are useful in the prophylaxis or treatment of HCV infections.

12 Claims, No Drawings

PHOSPHORAMIDATE DERIVATIVES OF NUCLEOSIDES

This application is a national stage application of PCT/EP2010/064413, filed Sep. 29, 2010, which claims priority benefit of Application No. EP 09171607.6 filed Sep. 29, 2009. The complete disclosures of the aforementioned related patent applications are hereby incorporated herein by reference for all purposes.

FIELD OF THE INVENTION

This invention relates to novel nucleoside compounds, which are inhibitors of the polymerase of hepatitis C virus (HCV) and their use in the treatment or prophylaxis of HCV.

BACKGROUND OF THE INVENTION

HCV is a single stranded, positive-sense RNA virus, with a genome of around 9,600 bases belonging to the Flaviviridae family of viruses in the hepacivirus genus. The NS5B region of the RNA polygene encodes a 65 kDa RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RNA-dependent RNA polymerase (RdRp) is absolutely essential for replication of the single-stranded, positive sense, RNA genome. This enzyme has elicited significant interest among medicinal chemists. Both nucleoside and non-nucleoside inhibitors of NS5B are known.

Nucleoside inhibitors can act either as a chain terminator or as a competitive inhibitor, which interferes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. In addition this limits the direct evaluation of nucleosides as inhibitors of HCV replication to cell-based assays capable of in situ phosphorylation.

Several research groups have attempted to develop nucleosides as inhibitors of HCV polymerase, but while a handful of compounds have entered clinical development, none have proceeded all the way to registration. Amongst the problems that HCV targeted nucleosides to date have encountered are toxicity, mutagenicity, lack of selectivity, poor efficacy, poor bioavailability, sub-optimal dosage regimes, and ensuing high pill burden and cost of goods.

Several patents and patent applications as well as scientific publications disclose nucleoside analogs having HCV inhibitory activity. WO 2007/020193 discloses phosphoramidate derivatives of certain nucleosides. WO 2008/043704 discloses 4-amino-1-((2R,3 S,4S,5R)-5-azido-4-hydroxy-5-hydroxymethyl-3-methyl-tetrahydro-furan-2-yl)-1H-pyrimidin-2-one and ester derivatives as HCV polymerase inhibitors. WO 2009/067409 discloses 2',4'-substituted nucleosides as antiviral agents.

There is a need for HCV inhibitors that may overcome the disadvantages of current HCV therapy such as side effects, limited efficacy, the emerging of resistance, and compliance failures, as well as improve the sustained viral response.

The present invention concerns phosphoramidate derivatives of 1-((2R,3S,4S,5R)-5-azido-4-hydroxy-5-hydroxymethyl-3-methyl-tetrahydrofuran-2-yl)-1H-pyrimidin-2,4-dione that are HCV inhibitors with useful properties as regards one or more of the parameters: antiviral efficacy, favorable profile of resistance development, lack of toxicity and genotoxicity, favorable pharmacokinetics and pharmacodynamics, such as an increased concentration of the mono or triphosphate analogs in the liver, increased absorption, in particular adsorption by liver cells, and ease of formulation and administration.

DESCRIPTION OF THE INVENTION

In accordance with the present invention, there is provided inhibitors of HCV polymerase, which can be represented by the formula I:

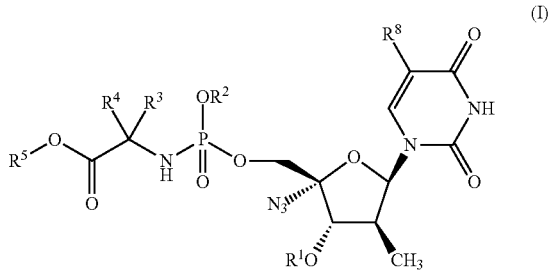

(I)

including any possible stereoisomers thereof, wherein:
$R^1$ is hydrogen, —C(=O)$R^6$ or —C(=O)CH$R^7$—NH$_2$;
$R^2$ is hydrogen; or $C_1$-$C_6$alkyl or phenyl, the latter being optionally substituted with 1, 2 or 3 substituents each independently selected from halo, $C_1$-$C_6$alkyl, $C_2$-$C_6$alkenyl, $C_1$-$C_6$alkoxy, hydroxy and amino; or $R^2$ is naphtyl; or $R^2$ is indolyl;
$R^3$ is hydrogen, $C_1$-$C_6$alkyl, benzyl;
$R^4$ is hydrogen, $C_1$-$C_6$alkyl, benzyl; or
$R^3$ and $R^4$ together with the carbon atom to which they are attached form $C_3$-$C_7$cycloalkyl;
$R^5$ is $C_1$-$C_{10}$alkyl, optionally substituted with $C_1$-$C_6$alkoxy; or $R^5$ is $C_3$-$C_7$cycloalkyl; benzyl; or phenyl, optionally substituted with 1, 2 or 3 substituents each independently selected from hydroxy, $C_1$-$C_6$alkoxy, amino, mono- and di$C_1$-$C_6$alkylamino;
$R^6$ is $C_1$-$C_6$alkyl;
$R^7$ is $C_1$-$C_6$alkyl;
$R^8$ is hydrogen or halogen;
or a pharmaceutically acceptable salt or solvate thereof.

A further aspect of the invention provides a compound of formula I or a pharmaceutically acceptable salt, hydrate, or solvate thereof, for use in the treatment or prophylaxis of HCV infection. Or there is provided the use of a compound of formula I or a pharmaceutically acceptable salt, hydrate, or solvate thereof, for the manufacture of a medicament for the treatment or prophylaxis of HCV infection. Representative HCV genotypes in the context of treatment or prophylaxis in accordance with the invention include genotype 1b (prevalent in Europe) or 1a (prevalent in North America). In another aspect, the invention provides a method for the treatment or prophylaxis of HCV infection, in particular of the genotype 1a or 1, said method comprising the administration of an amount effective to treat HCV or to provide prophylaxis against HCV

FURTHER DESCRIPTION OF THE INVENTION

One subgroup of compounds comprises compounds of formula I, or any of the subgroups of compounds mentioned herein, wherein $R^1$ is hydrogen. Another subgroup comprises compounds of formula I, or any of the subgroups of compounds mentioned herein, wherein $R^1$ is a $C_2$-$C_6$ acyl group, such as acetyl, pivaloyl or preferably isobutyryl. Another subgroup comprises compounds of formula I, or any of the subgroups of compounds mentioned herein, wherein $R^1$ is an α-aminoacyl group, stemming from an L-amino acid such as L-alanine, L-leucine, L-isoleucine or L-valine.

Another subgroup of compounds comprises those compounds of formula I, or any of the subgroups of compounds mentioned herein, wherein $R^2$ is phenyl optionally substituted with 1, 2 or 3 substituents independently selected from halo, $C_1$-$C_6$alkyl, and $C_2$-$C_4$alkenyl, or wherein $R^2$ is naphtyl. Of interest are compounds of formula I or any of the subgroups of compounds mentioned herein, wherein $R^2$ is phenyl, naphtyl or phenyl substituted with methyl, isopropyl and chloro, the latter more in particular being 3-methyl-4-chloro-6-isopropyl-phenyl. Another subgroup of compounds comprises compounds of formula I, or any of the subgroups of compounds mentioned herein, wherein $R^2$ is hydrogen.

In the compounds of formula I, or in any of the subgroups of compounds mentioned herein, the group —NH—C($R^3$)($R^4$)—CO— forms an amino acid residue, which includes natural and non-natural amino acid residues. Of particular interest are those amino acid residues wherein $R^3$ is hydrogen. Where in the latter instance $R^4$ is other than hydrogen, the configuration at the asymmetric carbon atom bearing $R^3$ and $R^4$ preferably is that of an L-amino acid. Examples of —NH—C($R^3$)($R^4$)—CO— are glycine (Gly), alanine (Ala), 1,1-dimethylglycine, valine (Val), isoleucine (Ile) and phenylalanine (Phe) residues, in particular the L-form such as L-Ala, L-Val, L-Ile, and L-Phe. An example of an amino acid residue wherein $R^3$ and $R^4$ together with the carbon atom to which they are attached form $C_3$-$C_7$cycloalkyl, is 1,1-cyclopropylamino acid.

One subgroup of compounds comprises compounds of formula I, or any of the subgroups of compounds mentioned herein, wherein $R^3$ is hydrogen or $C_1$-$C_6$alkyl, and $R^4$ is hydrogen or $C_1$-$C_6$alkyl; or wherein $R^3$ is hydrogen or $C_1$-$C_4$alkyl, and $R^4$ is hydrogen or $C_1$-$C_4$alkyl; or wherein $R^3$ is hydrogen or $C_1$-$C_4$alkyl, and $R^4$ is hydrogen. A particular subgroup amongst the foregoing is that wherein $R^4$ is hydrogen and wherein the carbon bearing $R^3$ and $R^4$ is in L-configuration. In one embodiment, in the compounds of formula I, or in any of the subgroups of the compounds of formula I, $R^3$ is methyl or a branched $C_1$-$C_6$alkyl, such as isopropyl or isobutyl, and $R^4$ is hydrogen, or wherein and $R^3$ is methyl and $R^4$ is hydrogen, or wherein $R^3$ is methyl and $R^4$ is methyl. Also of interest are the compounds of formula I, or any of the subgroups of compounds mentioned herein, wherein the group —NH—C($R^3$)($R^4$)—CO— forms —NH—CH$_2$—CO— (Gly), the L-isomer of —NH—CH(CH$_3$)—CO— (L-Ala), or —NH—C(CH$_3$)$_2$—CO— (α,α-dimethylglycyl); in particular L-Ala or α,α-dimethylglycyl, more in particular L-Ala.

One embodiment concerns the compounds of formula I, or any of the subgroups of compounds I mentioned herein, wherein $R^5$ is $C_1$-$C_{10}$alkyl optionally substituted with $C_1$-$C_4$alkoxy, or $R^5$ is $C_3$-$C_7$cycloalkyl (in particular $C_5$-$C_6$cycloalkyl), or benzyl, in particular wherein $R^5$ is methyl, ethyl, n-propyl, 2-butyl-pentyl, cyclopentyl, cyclohexyl, or benzyl. Of interest are $R^5$ groups wherein a $C_1$-$C_6$alkyl moiety, such as methyl or ethyl is substituted with an alkoxy group such as methoxy or ethoxy, for example $R^5$ is CH$_3$—O—CH$_2$—CH$_2$—.

One embodiment concerns the compounds of formula I, or any of the subgroups of compounds I mentioned herein, wherein $R^6$ is $C_1$-$C_4$alkyl, or wherein $R^6$ is isopropyl.

One embodiment concerns the compounds of formula I, or any of the subgroups of compounds I mentioned herein, wherein $R^7$ is $C_1$-$C_4$alkyl, or wherein $R^7$ is methyl; a further subgroup of compounds concerns those wherein $R^7$ is as specified herein and the —C(=O)CH$R^7$—NH$_2$ has the L-configuration.

One embodiment concerns the compounds of formula I, or any of the subgroups of compounds I mentioned herein, wherein $R^8$ is hydrogen or iodo; or $R^8$ is hydrogen.

A particular subgroup of compounds of formula I are those wherein:

$R^1$ is hydrogen;

$R^2$ is phenyl substituted with 1, 2 or 3 substituents independently selected from $C_1$-$C_6$alkyl, halo, and $C_2$-$C_4$alkenyl; —NH—C($R^3$)($R^4$)—CO— forms L-Ala or α,α-dimethylglycyl;

$R^5$ is $C_1$-$C_{10}$alkyl, $C_1$-$C_6$alkyl substituted with $C_1$-$C_6$alkoxy; $C_3$-$C_7$cycloalkyl, or benzyl;

$R^8$ is hydrogen or iodo.

Another particular subgroup of compounds of formula I are those wherein:

$R^1$ is hydrogen;

$R^2$ is phenyl, phenyl substituted with two $C_1$-$C_4$alkyl and with halo, or naphtyl; —NH—C($R^3$)($R^4$)—CO— forms L-Ala or α,α-dimethylglycyl;

$R^5$ is $C_1$-$C_{10}$alkyl, $C_1$-$C_4$alkyl substituted with $C_1$-$C_4$alkoxy, $C_5$-$C_6$cycloalkyl, or benzyl.

$R^8$ is hydrogen.

A particular subgroup of compounds of formula I are those wherein:

$R^1$ is hydrogen; $R^2$ is hydrogen; —NH—C($R^3$)($R^4$)—CO— forms L-Ala or α,α-dimethyl-glycyl; $R^5$ is $C_1$-$C_8$alkyl, $C_1$-$C_4$alkyl substituted with $C_1$-$C_4$alkoxy, cyclopentyl, cyclohexyl, or benzyl; $R^8$ is hydrogen.

A particular subgroup of compounds of formula I are those wherein:

$R^1$ is hydrogen; $R^2$ is hydrogen; —NH—C($R^3$)($R^4$)—CO— forms L-Ala; $R^5$ is $C_1$-$C_8$alkyl, cyclopentyl, cyclohexyl, or benzyl; $R^8$ is hydrogen.

A particular subgroup of compounds of formula I are compounds I-1 to I-35 listed in Table 1 hereinafter, including the pharmaceutically acceptable salts and solvates thereof.

The compounds of formula I have several chiral centers and are represented herein as a specific stereoisomer. This also applies to some of the intermediates used in the preparation of the compounds of formula I, which intermediates may contain one or more chiral centers. However, the compounds of formula I, or any of the intermediates used in their preparation that have at least one chiral center, may contain small amounts of the other stereoisomers, i.e. stereoisomers with different chirality at one or more of the asymmetric centers. The total amount of the other stereoisomers in particular does not exceed 25%, or 20%, or 10%, or 5%, or 2%, or 1%, or 0.5%, or 0.1% by weight.

Chirality may also be present in the substituents, such as, for instance chirality caused by the substituents in

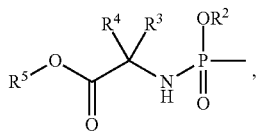

e.g. the $R^3$ and $R^4$ bearing carbon (where $R^3$ and $R^4$ are different), or the phosphorus atom. The phosphorus center can be present as $R_P$ or $S_P$, or a mixture of such stereoisomers, including racemates. Diastereoisomers resulting from the chiral phosphorus center and a chiral carbon atom may exist as well.

The absolute configuration at each of the chiral centers can be determined using art-known methods such as, for example, X-ray diffraction or NMR and/or by implication from starting materials of known stereochemistry. Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromate-graphic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromato-graphy, e.g. column chromatography.

The pharmaceutically acceptable addition salts comprise the therapeutically active non-toxic acid and base addition salt forms of the compounds of formula I. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxylbutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula I that contain an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" refers any solvates that the compounds of formula I as well as the salts thereof, may form. Such solvates are for example hydrates, alcoholates, e.g. ethanolates, propanolates, including n.propanolates and isopropanolates, and the like.

Some of the compounds of formula I may also exist in their tautomeric form. The uridine base is an example of such a form. Although not explicitly indicated in the above formula such forms are intended to be included within the scope of the present invention.

As used herein '$C_1$-$C_4$alkyl' as a group or part of a group defines saturated straight or branched chain hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. '$C_1$-$C_5$alkyl' encompasses $C_1$-$C_4$alkyl radicals and the higher homologues thereof having 5 carbon atoms such as, for example, 1-pentyl, 2-pentyl, 3-pentyl, 2-methyl-1-butyl, and the like. '$C_1$-$C_6$alkyl' encompasses $C_1$-$C_4$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl.

$C_1$-$C_{10}$alkyl encompasses $C_1$-$C_6$alkyl radicals and the higher homologues thereof having 7-10 carbon atoms, notably branched homologues such as 2-propylpentyl. Of interest amongst $C_1$-$C_{10}$alkyl is $C_1$-$C_8$alkyl (which encompasses $C_1$-$C_6$alkyl radicals and the higher homologues thereof having 7-8 carbon atoms) or $C_1$-$C_6$alkyl.

'$C_2$-$C_6$alkenyl' as a group or part of a group defines saturated straight or branched chain hydrocarbon radicals having from 1 to 6 carbon atoms and one double bond such as for example ethenyl, 1-propenyl, 2-propenyl, 1-butenyl, 2-butenyl, 3-butenyl, 2-methyl-l-propenyl, 2-methyl-2-propenyl, 4-pentenyl, 3-pentenyl, 5-hexenyl, 4-hexenyl, 3-hexenyl, and the like. One subgroup of $C_2$-$C_6$alkenyl includes the $C_2$-$C_6$alkenyl radicals in which the carbon with which the group is linked to the remainder of the molecule is saturated. Another subgroup are the $C_2$-$C_4$alkenyl, which are alkenyl radicals with two to four carbon atoms. Other subgroups of $C_2$-$C_6$alkenyl include the $C_2$-$C_6$alkenyl or the $C_2$-$C_4$alkenyl groups in which the carbon with which the group is linked to the remainder of the molecule is saturated.

'$C_1$-$C_4$alkoxy' refers to a radical —O—$C_1$-$C_4$alkyl wherein $C_1$-$C_4$alkyl is as defined above. $C_1$-$C_4$alkoxy radicals of interest include but are not limited to methoxy, ethoxy, n-propoxy and isopropoxy.

"$C_3$-$C_7$cycloalkyl" includes cyclopropyl, cyclobutyl, cyclopentyl, cyclohexyl and cycloheptyl. Of interest are cyclopropyl, cyclopentyl, and cyclohexyl.

"$C_2$-$C_6$acyl" as a group or part of a group defines a $C_1$-$C_5$alkyl group that is attached to a carbonyl group with a single bond, and includes, for instance, acetyl, propanoyl, butanoyl, isobutanoyl, pentanoyl, hexanoyl, pivanoyl, and the like. Nomenclature of the $C_2$-$C_6$acyl moieties listed above may be different such as, for instance, isobutanoyl may also be denoted as isobutyryl.

The term 'halo' is generic to fluoro, chloro, bromo and iodo.

As used herein, the term '(=O)' or 'oxo' forms a carbonyl moiety when attached to a carbon atom. It should be noted that an atom can only be substituted with an oxo group when the valency of that atom so permits.

It should be noted that the radical positions on any molecular moiety used in the definitions may be anywhere on such a moiety as long as it is chemically stable. When any variable occurs more than one time in any moiety, each definition is independent.

The present invention also includes isotope-labeled compounds of formula I or any subgroup of formula I, wherein one or more of the atoms is replaced by an isotope that differs from the one(s) typically found in nature. Examples of such isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; phosphorus, such as $^{31}$P and $^{32}$P, sulphur, such as $^{35}$S; fluorine, such as $^{18}$F; chlorine, such as $^{36}$Cl; bromine such as $^{75}$Br, $^{76}$Br, $^{77}$Br and $^{82}$Br; and iodine, such as $^{123}$I, $^{124}$I, $^{125}$I and $^{131}$I. Isotope-labeled compounds of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3$H or $^{14}$C is incorporated. For radio-imaging applications, a positron emitting isotope such as $^{11}$C, $^{18}$F, $^{13}$N or $^{15}$O will be useful. The incorporation of deuterium may provide greater metabolic stability, resulting in, e.g. an increased in vivo half life of the compound or reduced dosage requirements.

Whenever used herein, the terms "compounds of formula I", or "the present compounds" or "subgroups of compounds of formula I", or similar terms, are meant to include the compounds of formula I, or subgroups thereof, as well as their salts and solvates.

The compounds of formula I can be prepared by reacting a nucleoside derivative (1b) with a chlorophosphoramidate (1a) as outlined in scheme 1.

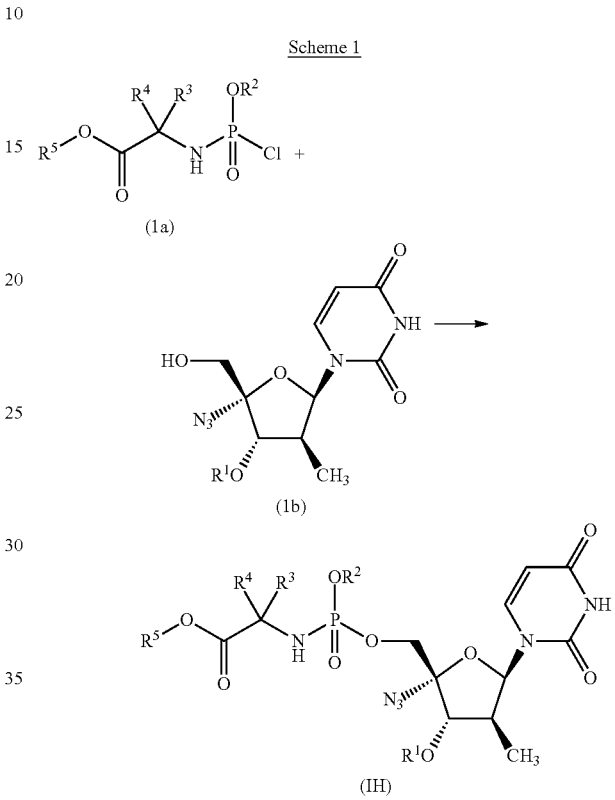

Condensation of nucleoside derivative (1b) with a chlorophosphoramidate (1a) conducted in a reaction-inert solvent such as an ether, e.g. diethylether, THF or MeTHF, or a halogenated hydrocarbon, e.g. dichloromethane, in the presence of a base such as a N-methylimidazole or the like, provides a phosphoramidate of formula (I). Alternatively, a Grignard reagent e.g. t-BuMgCl may be used as the base, in this case the reaction is conveniently performed in an ether solvent, e.g. THF or MeTHF.

Nucleoside derivatives 1b wherein $R^1$ is other than hydrogen can be prepared as illustrated in scheme 2.

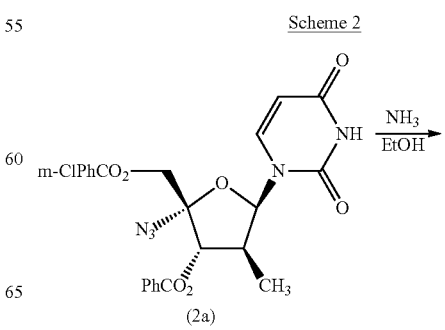

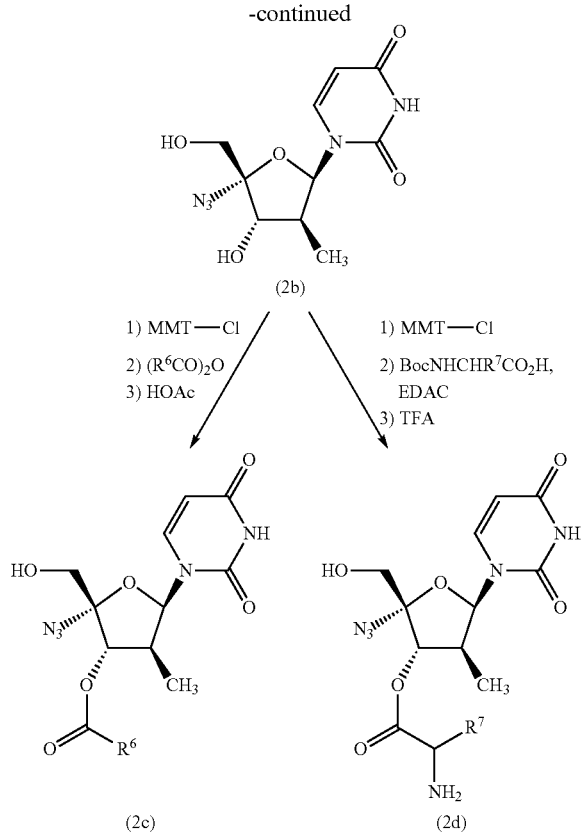

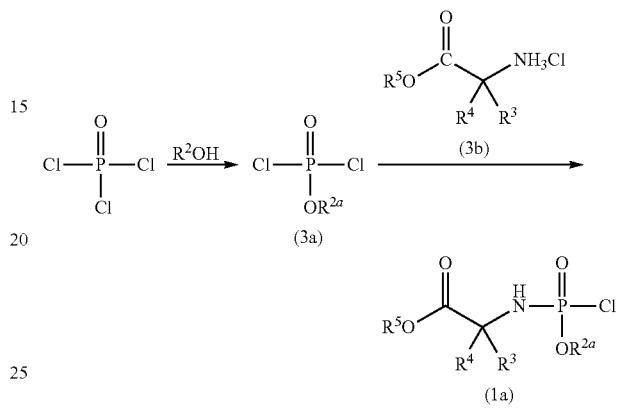

with the dihydroxy compound (2b) and introducing the desired 3'-substituent thereafter.

The chlorophosphoramidates (la) can be prepared by a two step sequence starting from phosphorusoxychloride, as illustrated in Scheme 3, wherein $R^{2a}$ has the same meaning as $R^2$ but is other than hydrogen, and $R^3$, $R^4$ and $R^5$ are as defined above.

Condensation of $POCl_3$ with an alcohol $R^{2a}OH$ in a reaction-inert solvent such as $Et_2O$ provides the alkyloxy or aryloxy phosphorodichloridate (3a). Subsequent reaction with an amino acid derivative (3b), wherein $R^5$ is as defined above, or $R^5$ may be a carboxyl acid protecting group that is removed and replaced by the desired $R^5$ group, provides the chlorophosphoramidate (la). These reactions are conducted in a reaction-inert solvent, such as the solvents mentioned above in relation to the preparation of the compounds of formula I.

The nucleoside derivatives (1b) wherein $R^1$ is H, can be obtained by hydrolysis of the 3' and 5' ester groups in the diester (2a) (prepared e.g. as described in WO 2008/043704) using an ester hydrolysis method, for instance by treatment with ammonia in ethanol. Nucleoside derivatives (1b) carrying a substituent at the 3' position i.e. where $R^1$ is —C(=O)$R^6$ or —C(=O)$CR^7$—$NH_2$, wherein $R^6$ and $R^7$ are as defined above, can be prepared from the diol nucleoside (2b) by a protection-acylation-deprotection sequence. For example, selective protection of the primary hydroxy group with a trityl or monomethoxy trityl (MMT) group, or the like, by treatment with a trityl-introducing agent, for example the halide such as the chloride, in the presence of a base such as pyridine, followed by acylation of the 3'-hydroxy group using the appropriate acylating conditions provides the 3'-acylated derivatives. Nucleosides (2c) carrying an ester group in the 3'-position i.e. $R^1$ in formula (1a) is —C(=O)$R^6$, are conveniently obtained by reaction of the 5'-protected nucleoside with an alkyl anhydride of formula ($R^6CO)_2O$ in the presence of a base such as pyridine or the like. Nucleosides (2d) carrying an amino acid in the 3'-position i.e. $R^1$ in formula (1a) is —C(=O)$CR^7$—$NH_2$, can be obtained by reaction of the 5'-protected nucleoside with an N-protected aliphatic amino acid in the presence of a suitable peptide coupling reagent such as EDAC or the like. Removal finally of the 5'-O-protecting group, and in case of $R^1$ being introduced as an N-protected amino acid, the N-protecting group, using the appropriate conditions according to the protecting group used, such as acidic treatment in the case of a trityl or monomethoxy trityl protecting group, then provides the 3'-acylated derivatives (2c) and (2d). The compounds of formula I wherein $R^1$ is —C(=O)$R^6$ or —C(=O)$CR^7$—$NH_2$ can alternatively be prepared by first condensing the chlorophosphoramidate (1a)

In a further aspect, the present invention concerns a pharmaceutical composition comprising a therapeutically effective amount of a compound of formula I, as specified herein, and a pharmaceutically acceptable carrier. A therapeutically effective amount in this context is an amount sufficient to act in a prophylactic way against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorraghic fever and encephalitis. A number of the compounds of this invention moreover are believed to be active against mutated strains of HCV.

Additionally, many of the compounds of this invention show a favorable pharmacokinetic profile and have attractive properties in terms of bioavailabilty, including an acceptable half-life, AUC (area under the curve) and peak values and lacking unfavorable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I and the pharmaceutically acceptable salts or solvates thereof, are useful in the treatment of individuals infected with a virus, particularly a virus that is HCV, and for the prophylaxis of viral infections, in particular HCV infections. In general, the compounds of the present invention may be useful in the treatment of warm-blooded animals infected with viruses, in particular flaviviruses such as HCV.

The compounds of the present invention may therefore be used as a medicine. The present invention also relates to the use of the compounds of the present invention in the manufacture of a medicament for the treatment or the prevention of a viral infection, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula I, as specified herein. Said use as a medicine or method of treatment comprises the systemic administration to virally infected subjects or to subjects susceptible to viral infections of an amount effective to combat the conditions associated with the viral infection, in particular HCV infection.

In general it is contemplated that an antiviral effective daily amount would be from 0.01 mg/kg to 500 mg/kg body weight, or from 0.1 mg/kg to 50 mg/kg body weight, or from 0.5 mg/kg to 5 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The invention also relates to a combination of a compound of formula I, a pharmaceutically acceptable salt, or a pharmaceutically acceptable solvate thereof, and another antiviral compound, in particular another anti-HCV compound. The term "combination" may relate to a product containing (a) a compound of formula I, as specified above, and (b) optionally another anti-HCV compound, as a combined preparation for simultaneous, separate or sequential use in treatment of HCV infections.

Anti-HCV compounds that can be used in such combinations include nucleoside or nun-nucleoside HCV polymerase inhibitors, HCV protease inhibitors, HCV helicase inhibitors, or HCV fusion inhibitors. Other agents that can be used in such combinations include interferon-α (IFN-α), pegylated interferon-α, and ribavirin.

Any of the above-mentioned combinations may be formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination.

The individual components of the combinations of the present invention can be administered separately at different times during the course of therapy or concurrently in divided or single combination forms. Preferably, the separate dosage forms are administered simultaneously.

The compounds of formula I, or the combinations described herein, including those with other anti-HCV agents, may also be combined with an agent that has a positive effect on drug metabolism and/or pharmacokinetics that improve bioavailabilty, e.g. ritonavir or a pharmaceutically acceptable salt thereof. The ritonavir may be used as separate formulation, or may be co-formulated with one or more of the active agents of the combinations of the present invention. The weight ratio of the compound of formula I to ritonavir may be in the range of from about 10:1 to about 1:10, or from about 6:1 to about 1:6, or from about 1:1 to about 10:1, or from about 1:1 to about 6:1, or from about 1:1 to about 4:1, or from about 1:1 to about 3:1, or from about 1:1 to about 2:1.

EXAMPLES

The following examples are meant to illustrate the invention and not to limit its scope thereto. The symbol Bn represents benzyl.

Example 1

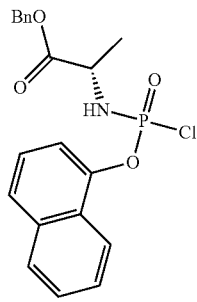 [SMILES: C[C@H](NP(=O)(Cl)Oc1cccc2ccccc12)C(=O)OCc1ccccc1]

3 g of 1-naphthol were loaded into a 3-neck flask and dissolved in Et$_2$O (60 mL) under N$_2$. To the solution was added POCl$_3$ (1 eq.) and the resulting solution cooled to −78° C. To the cold solution was added dropwise (over approx. 15min.) Et$_3$N (1 eq.). The reaction was allowed to reach room temperature overnight and then the white solid was filtered off, washed with Et$_2$O while avoiding contact with moisture. The combined ether phases were concentrated in vacuum, the residue re-dissolved in CH$_2$Cl$_2$ (120 mL) under N$_2$. To this solution was added L-Alanine benzyl ester hydrochloride (1 eq.) and the mixture cooled to −78° C. To this was then added dropwise (over approx. 45 min) Et$_3$N (1 eq.). The reaction was allowed to reach room temperature overnight. The solvent was removed in vacuum, avoiding contact with moisture and the residue passed through dry silica-gel eluting with EtOAc/heptane: 7/3. The fractions containing the product were concentrated in vacuum avoiding contact with moisture and the residue dissolved in dry THF to obtain a standard solution of approximate concentration used as such in the next reaction.

Example 2

Preparation of Phosphorochloridates

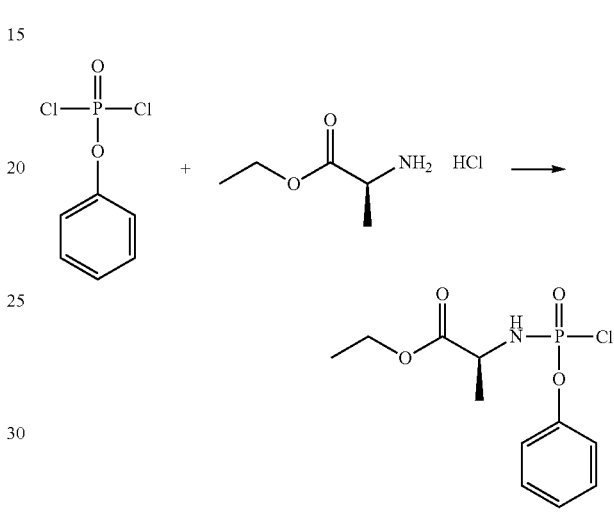

To a stirred solution of L-Alanine ethyl ester hydrochloride salt (5 g, 32.5 mmol, dried in vaccum for 48 h) in dichloromethane (50 mL) at approx -78° C. was dropwise added a solution of phenyl dichlorophosphate (5.7 g, 27 mmol, 4.05 ml) in dichloromethane (20 ml) over 5 minutes. To the resulting solution was added a solution of triethylamine (8.2 g, 81 mmol, 11.3 mL) in dichloromethane (20 mL) during 30 min. The obtained solid was slowly allowed to reach room temperature over 2 h, then the reaction mixture was applied directly onto column. Column chromatography (diam: 7 cm, SiO$_2$: 100 g, Packing eluent: ethyl acetate in i-Hexane 20%) of the residue using ethyl acetate in i-Hexane (stepwise gradient 20-30%) gave separation from byproducts such as phosphordiamidates. Appropriate fractions (monitored by TLC: i-Hex-EtOAc 3:2, product comes first as baseline spots, followed by diamidates which migrates on the TLC plate) were concentrated giving (2S)-ethyl 2-(chloro(phenoxy)phosphorylamino)-propanoate, a colorless oil (2.16 g, 7.4 mmol, 27%). The product was diluted with dichloromethane into a 0.25 M stock solution and could be kept in the freezer for up to a month. NMR data (400 MHz, 298 K, CDCl$_3$): $^1$H, δ 1.23-1.37 (m, 3 H), 1.52 (2d, 3 H), 4.08-4.37 (m, 4 H), 7.21-7.29 (m, 3 H), 7.37 (m, 2 H). $^{31}$P, δ 7.60 and 7.96 (2s, no P standard used).

The phosphochloroamidate intermediates of the compounds in Table 1 were prepared analogously.

Example 3

Compounds I-1 to I-35 (see Table 1) were synthesized using a method as described herebelow. In most cases, after purification, the compounds were obtained as mixtures of diastereomers with a racemic configuration at the phosphorous atom. In case where the diastereomers could be separated, no assignment of absolute configuration was done.

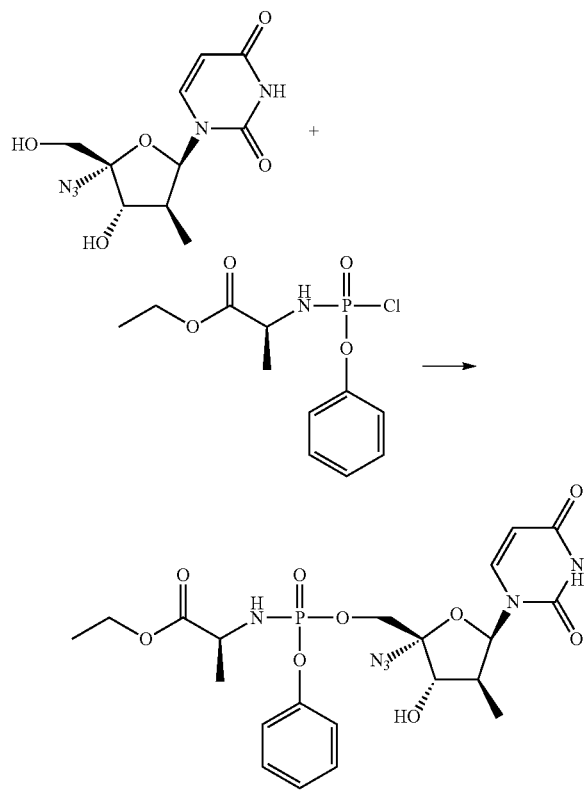

To a solution of 1-(5-Azido-4-hydroxy-5-hydroxymethyl-3-methyl-tetrahydro-furan-2-yl)-1H-pyrimidine-2,4-dione (0.88 g, 3.1 mmol) in dichloromethane (17 mL) and N-methyl-imidazole (0.76 g, 9.3 mmol, 0.74 ml) at approx −70° C. was dropwise added (2S)-ethyl 2-(chloro(phenoxy)phosphorylamino)propanoate (16 mL of a 0.25 M solution in dichloromethane) over 35 min while maintaining the temperature between −70 to −60° C. The reaction mixture was then slowly allowed to warm to 5-10° C. and was monitored by TLC (9:1 and 95:5 dichloromethane-methanol, UV detection). After a total of 130 min the reaction mixture was concentrated onto silica. The residue was purified by column chromatography (diam: 4 cm, SiO$_2$: 70 g, packing eluent: dichloromethane) using a stepwise gradient of methanol in dichloromethane (0-10%).

In this case, first a mixture of 3'-, 3',5'- and a single isomer of 5'-phosphoramidate eluted, then a diastereomeric mixture of 5'-phosphoramidates followed by a single isomer of 5'-phosphoramidate and last unreacted nucleoside (0.3 g, 1.06 mmol). Further purification of the material using prep-LC (Column: Phenomex Synergi 10 u, MAX-RP, 80A, size: 100×30 mm, Flow: 25 ml/min, Gradient: 30-60% acetonitrile in water over 20 min) gave separation of the unwanted disubstituted nucleosides and 3'-regioisomers from the desired 5'-phosphoramidates. Appropriate fractions were concentrated and lyophilized from dioxane then divided into the following residues: the first eluting 5'-diastereomer as a white powder (27 mg, 0.05 mmol, 2%), the 5'-diastereomeric mixture as a white solid (0.35 g, 21%) and the second eluting diastereomer as a white solid (33 mg, 2%).

NMR data of the first eluting diastereomer (400 MHz, 298 K, CDCl$_3$): $^1$H, δ 0.94 (d, 3 H), 1.26 (t, 3 H), 1.38 (d, 3 H), 2.74 (m, 1 H), 3.75 (d, 1 H, NH), 3.84-4.25 (m, 4 H, H-3', α-H, CH$_3$CH$_2$O), 4.37 (dd, 1 H, H-5'), 4.48 (dd, 1 H, H-5"), 5.59 (d, 1 H), 6.40 (brs, 1 H, H-1'), 7.17-7.39 (m, 6 H), 9.15 (s, 1 H, NH). $^{31}$P, δ 3.44 (s, no internal P standard used). LR-MS: Calcd for C$_{21}$H$_{27}$N$_6$O$_9$P: 539.16. Found: 539.12 [M+H].

NMR data of second eluting diastereomer (400 MHz, 298 K, CDCl$_3$): $^1$H, δ 1.01 (d, 3 H), 1.26 (t, 3 H), 1.38 (d, 3 H), 2.77 (m, 1 H), 3.92-4.24 (m, 5 H, NH, H-3', α-H, CH$_3$CH$_2$O), 4.42 (d, 2 H, H-5' and H-5"), 5.67 (d, 1 H), 6.41 (brs, 1 H, H-1'), 7.16-7.43 (m, 6 H). LR-MS: Calcd for C$_{21}$H$_{27}$N$_6$O$_9$P: 539.16. Found: 539.12 [M+H].

The first eluting diastereomer is designated diastereomer 1, and the second eluting diastereomer is designated diastereomer 2.

NMR data of other selected examples:

Compound I-2
Enantiopure Compound
$^1$H-NMR (400 MHz, CDCl$_3$) δ ppm 1.00 (d, J=7.0 Hz, 3 H) 1.18-1.22 (m, 6 H) 1.43 (d, J=6.8 Hz, 3 H) 2.28 (s, 3 H) 2.68-2.81 (m, 1 H) 3.17 (spt, J=6.9 Hz, 1 H) 3.69 (br. s., 1 H) 3.97-4.09 (m, 2 H) 4.14 (t, J=10.8 Hz, 1 H) 4.39 (d, J=8.6 Hz, 2 H) 5.14 (d, J=12.3 Hz, 1 H) 5.17 (d, J=12.3 Hz, 1 H) 5.67 (d, J=8.0 Hz, 1 H) 6.38 (br. s., 1 H) 7.21-7.39 (m, 8 H) 8.99 (br. s., 1 H)

Compound I-6
Diastereoisomeric Mixture
$^1$H-NMR (500 MHz, 298 K, DMSO-d$_6$): $^1$H, δ 0.85 (m, 3 H, 2'β-CH$_3$), 1.21 (d, 3 H, CH$_3$CH-), 1.47-1.75 (m, 8 H, 4 x CH$_2$), 2.63 (m, 1 H, H-2'), 3.79 (m, 1 H, CH$_3$CH—), 3.98 (brs, 1 H, H-3'), 4.38 (m, 2 H, H-5',5"), 5.02 (m, 1 H, (—CH$_2$)$_2$—CH—O), 5.55 (m, 1 H, H-5), 5.92 (m, 1 H, OH-3'), 6.13 (m, 1 H, —NH—P), 6.29 (brs, 1 H, H-1'), 7.20 (m, 3 H, Ar—H), 7.36 (m, 2 H, Ar—H), 7.52 (dd, 1 H, H-6), 11.46 (s, 1 H, O=C—NH—C=O)

Compound I-13
Diastereoisomeric Mixture (6:4)
$^1$H-NMR (500 MHz, 298 K, CDCl$_3$): δ 0.93 (m, 3 H, CH$_3$CH$_2$—), 1.03 (d, 3 H, 2'β-CH$_3$), 1.37 (m, 2 H, CH$_3$CH$_2$—), 1.51-1.69 (m, 8 H, (CH$_3$)$_2$C and —CH$_2$CH$_2$CH$_2$O—), 2.75 (m, 1 H, H-2'), 3.61 (d, —NH—P major), 3.74 (d, —NH—P minor), 3.88-4.20 (m, 3 H, H-3' and —CH$_2$CH$_2$O—), 4.30-4.51 (m, 2 H, H-5',5"), 5.54 (d, H-5 minor), 5.66 (d, H-5 major), 6.39 (brs, 1 H, H-1'), 7.10-7.47 (m, 6 H, Ar—H and H-6), 8.67 (brs, 1 H, O=C—NH—C=O).

Compound I-19
Enantiopure Compound
$^1$H NMR (400 MHz, CDCl$_3$) δ 0.98 (d, J=6.8 Hz, 3 H) 1.16-1.22 (m, 6 H) 1.42 (d, J=7.2 Hz, 3 H) 2.28 (s, 3 H) 2.69-2.81 (m, 1 H) 3.15 (spt, J=6.9 Hz, 1 H) 3.63 (br. s., 1 H) 3.87 (t, J=10.4 Hz, 1 H) 3.97-4.07 (m, 1 H) 4.08-4.18 (m, 1 H) 4.33-4.40 (m, 1 H) 4.43-4.49 (m, 1 H) 5.14 (d, J=12.3 Hz, 1 H) 5.19 (d, J=12.3 Hz, 1 H) 5.54 (d, J=8.1 Hz, 1 H) 6.39 (br. s., 1 H) 7.07 (d, J=8.1 Hz, 1 H) 7.24 (s, 1 H) 7.25 (s, 1 H) 7.30-7.40 (m, 5 H) 8.75 (br. s., 1 H)

Compound I-24
Diastereoisomeric Mixture (6:4)
$^1$H NMR (400 MHz, CDCl$_3$) δ ppm 0.99 (d, J=7.0 Hz, 1.2 H) 1.03 (d, J=6.8 Hz, 1.8 H) 1.20-1.24 (m, 6 H) 1.28 (t, J=7.1 Hz, 1.2 H) 1.40-1.44 (m, 3 H) 2.30 (s, 1.2 H) 2.31 (s, 1.8 H) 2.71-2.83 (m, 1 H) 3.18 (dq, J=13.7, 7.0 Hz, 1 H) 3.58 (d, J=6.8 Hz, 0.6 H) 3.69 (d, J=6.8 Hz, 0.4 H) 3.79 (t, J=10.5 Hz, 0.4 H) 3.89-4.11 (m, 2.6 H) 4.13-4.27 (m, 2 H) 4.35-4.52 (m, 2 H) 5.55 (d, J=8.0 Hz, 0.4 H) 5.68 (d, J=8.2 Hz, 0.6 H) 6.40 (br. s., 1 H) 7.09 (d, J=8.2 Hz, 0.6 H) 7.24 (s, 1 H) 7.25 (s, 1 H) 7.29 (d, J=8.0 Hz, 0.4 H) 8.60 (br. s., 1 H)

Compound I-25

Diastereoisomeric Mixture $^1$H NMR (400 MHz, DMSO-$d_6$) δ ppm 0.86 (br. s., 3 H) 1.27 (d, J=6.3 Hz, 3 H) 2.55-2.63 (m, 1 H) 3.85-4.19 (m, 4 H) 4.33-4.51 (m, 2 H) 5.02-5.13 (m, 2 H) 6.13-6.28 (m, 1 H) 7.13-7.37 (m, 10 H) 7.91 (br. s., 1 H) 8.40 (br. s., 1 H)

Compound I-35

Diastereoisomeric Mixture $^1$H NMR (400 MHz, DMSO-$d_6$) δ ppm 0.77-0.96 (m, 6 H), 1.21-1.34 (m, 2 H), 1.39 (d, J=15.41 Hz, 6 H), 1.45-1.58 (m, 2 H), 2.54-2.66 (m, 1 H), 3.91-4.05 (m, 2 H), 4.15 (br. s., 1 H), 4.27-4.62 (m, 2 H), 5.66-6.04 (m, 2 H), 6.18 (br. s., 1 H), 7.08-7.27 (m, 3 H), 7.35 (m, J=7.00, 7.00, 7.00 Hz, 2 H), 7.95 (br. s., 1 H), 11.84 (br. s., 1 H)

Example 4

Preparation of Compounds werein $R^2$=H.

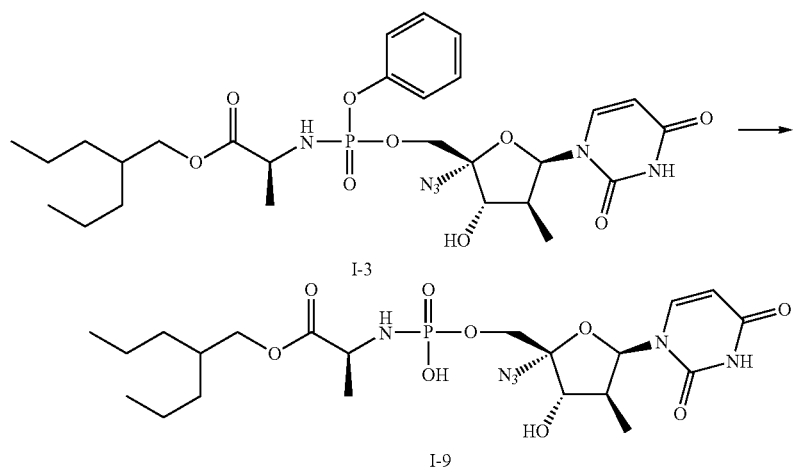

A solution of I-3 (234 mg, 0.38 mmol) and NH$_4$F (235 mg, 6.46 mmol) in isopropanol (9 ml) and water (9 ml) was heated to 95° C. HPLC showed completion of the reaction after appr. 1 h. After evaporation the crude material was purified with preparative LC-MS yielding 129 mg (59%) of I-9. Prep LC conditions: ColumnL Gemini-NX, 5 μ, C18, 110A Mobile phase: MeOH/H$_2$O (10 mmol NH$_4$Ac): 60/40 to 80/20 in 8 min. $^1$H-NMR data (500 MHz, 298 K, DMSO-$d_6$): δ 0.84 (m, 9 H, 2'β-CH$_3$ and 2×CH$_3$), 1.18-1.30 (m, 11 H, —CHCH$_3$ and 4×CH$_2$), 1.61 (m, 1 H, —CH(CH$_2$)$_3$), 2.60 (m, 1 H, H-2'), 3.23 (—NH—P), 3.71 (m, 1 H, —CHCH$_3$), 3.85-4.06 (m, 5 H, H-5',5", H-3', —CHCH$_2$O—), 5.60 (d, 1 H, H-5), 6.18 (brs, 1 H, H-1'), 7.68 (d, 1 H, H-6).

Biological Examples

Replicon Assay

The compounds of formula I are examined for activity in the inhibition of HCV RNA replication in a cellular assay. The assay demonstrates that the compounds of formula I exhibit activity against HCV replicons functional in a cell culture. The cellular assay can be based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. The Bartenschlager replicon assays are available commercially from ReBLikon GmbH in Mainz, Germany.

In essence, the method is as follows.

The assay utilized the stably transfected cell line Huh-7 luc/neo (hereafter referred to as Huh-Luc). This cell line harbors an RNA encoding a bicistronic expression construct comprising the wild type NS3—NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in well plates in the presence of the test and control compounds, which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC$_{50}$ values were then calculated, which value represents the amount of the compound required to decrease by 50% the level of detected luciferase activity, or more specifically, the ability of the genetically linked HCV replicon RNA to replicate. Where a compound of formula (I) was tested more than once in the replicon assay, the average of all test results is given in Table 1.

The compounds listed in the following table are racemic mixtures of the phosphorous enantiomers (which can also be referred to as "diastereoisomeric mixture"). In a number of instances these enantiomers were separated without determining the exact stereochemistry of the substituents on the phosphorous atom. Such compounds are indicated as diastereomer 1 (for the first eluting diastereomer) or 2 (for the second eluting diastereomer). In some cases diastereoisomeric mixtures were obtained that are enriched with one of the diastereoisomers.

TABLE 1

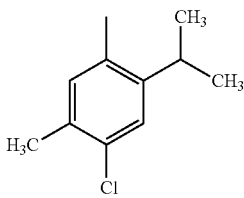

| Co. no. | $R^2$ | $R^3$ | $R^4$ | $R^5$ | $EC_{50}$ 1b ET (μM) | $CC_{50}$ Huh-7 (μM) | LC-MS result [M + H]+ |
|---|---|---|---|---|---|---|---|
| I-1 | phenyl | $CH_3$ | H | benzyl | 5.95 | >100 | 601.1 |
| I-2 | 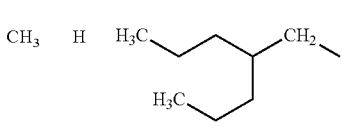 Diastereomer 1 | $CH_3$ | H | benzyl | 6.10 | 29.5 | 691 + 693 |
| I-3 | phenyl | $CH_3$ | H | 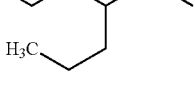 | 8.06 | 30.7 | 623.1 |
| I-4 | phenyl | $CH_3$ | H | butyl | 9.33 | >98.3 | 567.1 |
| I-5 | phenyl | $CH_3$ | H | pentyl | 9.48 | >98.3 | 581.3 |
| I-6 | phenyl | $CH_3$ | H | cyclopentyl | 10.47 | >98.3 | 579.3 |
| I-7 | phenyl | $CH_3$ | H | cyclohexyl | 11.21 | >98.3 | 593.1 |
| I-8 | phenyl Diastereomer 1 | $CH_3$ | H | ethyl | 11.95 | >98.3 | 539.1 |
| I-9 | H | $CH_3$ | H | 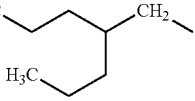 | 15.81 | | 547.2 |
| I-10 | phenyl | $CH_3$ | H | propyl | 12.87 | >98.3 | 553.1 |
| I-11 | naphtyl | $CH_3$ | H | benzyl | 13.83 | >100 | 649 (M − H)− |
| I-12 | phenyl | $CH_3$ | $CH_3$ | benzyl | 13.92 | >100 | 615.1 |
| I-13 | phenyl | $CH_3$ | $CH_3$ | butyl | 13.13 | 88.5 | 581.1 |
| I-14 | phenyl | $CH_3$ | H | i-propyl | 14.86 | >100 | 553.1 |
| I-15 | 4-chlorophenyl | $CH_3$ | H | (isohexyl group, $H_3C$, $H_3C$, $CH_2$) | 15.33 | >100 | 657 + 659 |
| I-16 | phenyl Diastereomeric mixture | $CH_3$ | H | ethyl | 16.38 | >98.3 | 539.1 |

TABLE 1-continued

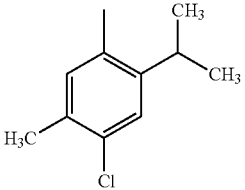

| Co. no. | R² | R³ | R⁴ | R⁵ | EC₅₀ 1b ET (μM) | CC₅₀ Huh-7 (μM) | LC-MS result [M + H]+ |
|---|---|---|---|---|---|---|---|
| I-17 | phenyl Diastereomer 2 | CH₃ | H | ethyl | 17.30 | >98.3 | 539.1 |
| I-18 | phenyl | CH₃ | H | methyl | 26.96 | >98.3 | 525.1 |
| I-19 | 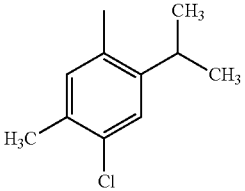 Diastereomer 2 | CH₃ | H | benzyl | 27.63 | 47.2 | 691 – 693 |
| I-20 | phenyl | ethyl | H | butyl | 28.01 | >73.9 | 581.1 |
| I-21 | phenyl | ethyl | H | benzyl | 29.15 | 81.8 | 615.1 |
| I-22 | 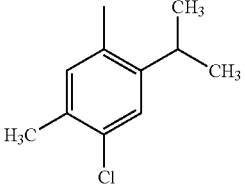 Diastereomeric mixture | CH₃ | H | benzyl | 31.73 | 60.5 | 691 – 693 |
| I-23 | phenyl | CH₃ | H | CH₃—O—(CH₂)₂— | 32.10 | >98.3 | 567.1 [M – H] |
| I-24 | (2,4-dimethyl-5-chloro-isopropylphenyl) | CH₃ | H | ethyl | 37.67 | 55.0 | 629 – 631 |
| I-26 | phenyl | ethyl | H | methyl | 74.67 | >98.3 | 539.0 |
| I-27 | H | ethyl | H | i-propyl | >98.36 | | 491.0 |
| I-28 | phenyl | CH₃ | CH₃ | i-propyl | >98.36 | >98.36 | 567.1 |
| I-29 | H | ethyl | H | methyl | >98.36 | >98.36 | 463.1 |
| I-30 | H | CH₃ | H | propyl | >98.36 | >98.36 | 477.1 |
| I-31 | phenyl | CH₃ | H | t-butyl | >98.36 | >98.36 | 567.2 |
| I-32 | H | CH₃ | CH₃ | butyl | >98.36 | | 505.1 |
| I-33 | H | ethyl | H | benzyl | >98.36 | | 539.1 |
| I-34 | phenyl | ethyl | H | i-propyl | >98.36 | >98.36 | 567.1 |
| I-35 | phenyl | H | CH₃ | butyl | 49.89 | >98.3 | 707 |

In the above table, the group

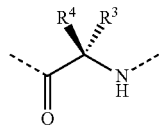

wherein $R^3$ is $CH_3$ and $R^4$ is hydrogen, i.e.

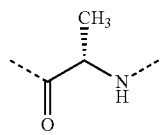

represents -L-Ala-(L-alanyl)

| Co. No. | Structure | $EC_{50}$ 1b ET (μM) | $CC_{50}$ Huh-7 (μM) | LC-MS result [M + H]+ |
|---|---|---|---|---|
| I-25 | 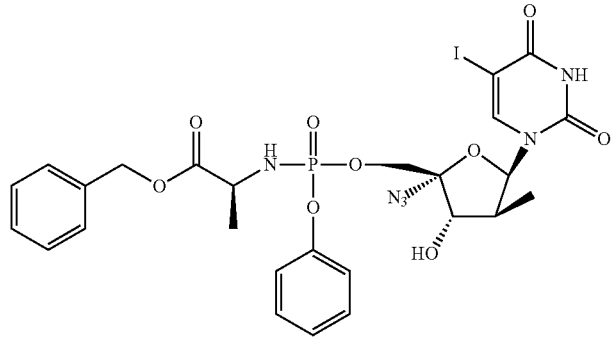 [SMILES: C[C@@H]1[C@H](n2cc(I)c(=O)[nH]c2=O)O[C@@](COP(=O)(N[C@@H](C)C(=O)OCc2ccccc2)Oc2ccccc2)(N=[N+]=[N-])[C@H]1O] | 57.32 | >98.3 | 725.1 [M − H]− |

Inhibition Assay

Enzyme assays with various HCV NS5 constructs are described in EP 842276, EP 858833 and EP1037974. Polymerase assays typically employ the polymerase, a pool of nucleotide triphosphates and a primer/template. Nucleoside test compounds must generally be synthetically phosphorylated to the triphosphate, which is an arduous procedure. EP1350276 describes a reporter gene assay intended to avoid that disadvantage of isolated enzyme assays.

Triphosphate Accumulation

Compounds can be assayed for intracellular acccumulation of the antivirally active triphosphate species, for example by administering the compound to appropriate human cells such as hepatocytes, incubation to allow intracellular cellular kinases to trisphosphorylate the phosphate group and cell lysis and extraction.

The invention claimed is:

1. A compound the formula I:

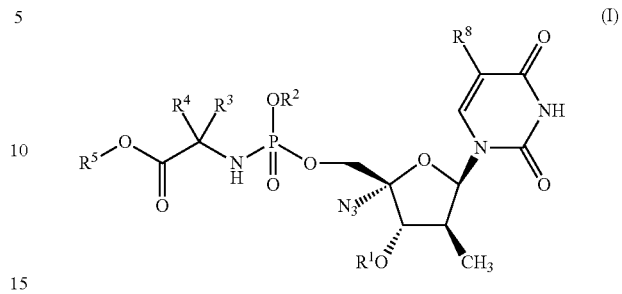

or a stereoisomeric form thereof, wherein:

$R^1$ is hydrogen, —C(=O)$R^6$ or —C(=O)CH$R^7$—NH$_2$;

$R^2$ is hydrogen; or $C_1$-$C_6$alkyl or phenyl, the latter being optionally substituted with 1, 2 or 3 substituents each independently selected from halo, $C_1$-$C_6$alkyl, $C_2$-$C_6$alkenyl, $C_1$-$C_6$alkoxy, hydroxy and amino; or $R^2$ is naphtyl; or $R^2$ is indolyl;

$R^3$ is hydrogen, $C_1$-$C_6$alkyl, benzyl;

$R^4$ is hydrogen, $C_1$-$C_6$alkyl, benzyl; or $R^3$ and $R^4$ together with the carbon atom to which they are attached form $C_3$-$C_7$cycloalkyl;

$R^5$ is $C_1$-$C_{10}$alkyl, optionally substituted with $C_1$-$C_6$alkoxy; or $R^5$ is $C_3$-$C_7$cycloalkyl; benzyl; or phenyl, optionally substituted with 1, 2 or 3 substituents each independently selected from hydroxy, $C_1$-$C_6$alkoxy, amino, mono- and di$C_1$-$C_6$alkylamino;

$R^6$ is $C_1$-$C_6$alkyl;

$R^7$ is $C_1$-$C_6$alkyl;

$R^8$ is hydrogen or halogen;

or a pharmaceutically acceptable salt thereof.

2. A compound according to claim 1, wherein $R^1$ is hydrogen.

3. A compound according to claim 1, wherein $R^2$ is Phenyl optionally substituted with 1, 2 or 3 substituents independently selected from halo, $C_1$-$C_6$alkyl, and $C_2$-$C_4$alkenyl, or wherein $R^2$ is naphtyl.

4. A compound according to claim 1, wherein $R^3$ is Hydrogen and $R^4$ is methyl or wherein $R^3$ is methyl and $R^4$ is hydrogen, or wherein $R^3$ and $R^4$ are both methyl.

5. A compound according to claim 1, wherein $R^5$ is $C_1$-$C_{10}$alkyl, $C_{3-7}$cycloalkyl; or benzyl.

6. A compound according to claim 1, wherein $R^8$ is hydrogen.

7. A compound according to claim 1, wherein $R^3$ is hydrogen or $C_1$-$C_6$alkyl, and $R^4$ is hydrogen or $C_1$-$C_6$alkyl.

8. A compound according to claim 1, wherein $R^1$ is hydrogen; $R^2$ is hydrogen; —NH—C($R^3$)($R^4$)—CO— forms L-Ala or α,α-dimethylglycyl; $R^5$ is $C_1$-$C_8$alkyl, $C_1$-$C_4$alkyl substituted with $C_1$-$C_4$alkoxy, cyclopentyl, cyclohexyl, or benzyl; $R^8$ is hydrogen.

9. A compound according to claim 1, wherein $R^1$ is hydrogen; $R^2$ is hydrogen; —NH—C($R^3$)($R^4$)—CO— forms L-Ala; $R^5$ is $C_1$-$C_8$alkyl, cyclopentyl, cyclohexyl, or benzyl; $R^8$ is hydrogen.

10. A compound according to claim 9, wherein $R^5$ is cyclopentyl or cyclohexyl.

11. A pharmaceutical composition comprising a compound of formula I as defined in claim 1 and a pharmaceutically acceptable carrier.

12. A pharmaceutical composition according to claim 11, further comprising at least one additional HCV antiviral.

* * * * *